US00PP18951P2

(12) United States Plant Patent
Bergman

(10) Patent No.: US PP18,951 P2
(45) Date of Patent: Jun. 17, 2008

(54) *AZALEA* PLANT NAMED 'YBAZ-2147'

(50) Latin Name: *Rhododendron hybrida*
Varietal Denomination: YBAZ-2147

(75) Inventor: Wendy R. Bergman, Lehigh Acres, FL (US)

(73) Assignee: Yoder Brothers Inc., Barberton, OH (US)

( * ) Notice: Subject to any disclaimer, the term of this patent is extended or adjusted under 35 U.S.C. 154(b) by 0 days.

(21) Appl. No.: 11/725,802

(22) Filed: Mar. 20, 2007

(51) Int. Cl.
*A01H 5/00* (2006.01)

(52) U.S. Cl. ..... Plt./239

(58) Field of Classification Search ..... Plt./239
See application file for complete search history.

*Primary Examiner*—Annette H Para
(74) *Attorney, Agent, or Firm*—C. A. Whealy

(57) ABSTRACT

A new and distinct cultivar of *Azalea* plant named 'YBAZ-2147', characterized by its dark green-colored leaves that do not abscise during the cooling and forcing periods; uniform and outwardly spreading plant habit; freely branching habit; uniform and freely flowering habit; relatively rapid flowering response; large coral pink-colored flowers; fully double flower form; and excellent postproduction longevity with plants maintaining good flower substance for about five weeks in an interior environment.

2 Drawing Sheets

Botanical designation: *Rhododendron hybrida.*
Cultivar denomination: 'YBAZ-2147'.

BACKGROUND OF THE INVENTION

The present Invention relates to a new and distinct cultivar of *Azalea*, botanically known as *Rhododendron hybrida,* an evergreen greenhouse-forcing type *Azalea*, and hereinafter referred to by the name 'YBAZ-2147'.

The new *Azalea* is a product of a planned breeding program conducted by the Inventor in Alva, Fla. The objective of the breeding program is to create new *Azalea* varieties having uniform plant habit, profuse and uniform flowering response, dark green foliage, good foliage retention during the cooling and forcing periods, resistance to *Cylindrocladium* and excellent postproduction longevity.

The new *Azalea* is a naturally-occurring whole plant mutation of the *Rhododendron hybrida* cultivar YBAZ1812, disclosed in U.S. Plant Pat. No. 16,499. The new Chrysanthemum was discovered and selected by the Inventor as a single flowering plant within a population of plants of the cultivar YBAZ1812 in June, 2002, in Alva, Fla. The selection of this plant was based on its attractive flower color.

Asexual reproduction of the new *Azalea* by terminal cuttings in a controlled environment in Alva, Fla. since November, 2002, has shown that the unique features of this new *Azalea* are stable and reproduced true to type in successive generations.

SUMMARY OF THE INVENTION

The new *Azalea* has not been observed under all possible environmental conditions. The phenotype may vary somewhat with variations in environment such as temperature, daylength and/or light intensity without, however, any variance in genotype. The following traits have been repeatedly observed and are determined to be the unique characteristics of 'YBAZ-2147'. These characteristics in combination distinguish 'YBAZ-2147' as a new and distinct cultivar:

1. Dark green-colored leaves that do not abscise during the cooling and forcing periods.
2. Uniform and outwardly spreading plant habit.
3. Freely branching habit.
4. Uniform and freely flowering habit.
5. Relatively rapid flowering response; plants begin flowering about 29 days after cooling treatment.
6. Large coral pink-colored flowers.
7. Fully double flower form.
8. Excellent postproduction longevity with plants maintaining good flower substance for about five weeks in an interior environment.

Plants of the new *Azalea* differ from plants of the parent, the cultivar YBAZ1812, primarily in flower color as plants of the cultivar YABZ1812 have light coral pink-colored flowers with darker pink-colored flecks and stripes.

Plants of the new *Azalea* can be compared to the plants of the cultivar Promise, disclosed in U.S. Plant Pat. No. 11,920. In side-by-side comparisons conducted in Alva, Fla., plants of the new *Azalea* differed from plants of the cultivar Promise in the following characteristics:

1. Plants of the new *Azalea* had smaller flowers than plants of the cultivar Promise.
2. Plants of the new *Azalea* and the cultivar Promise differed in flower color as plants of the cultivar Promise had lighter coral pink-colored flowers.

BRIEF DESCRIPTION OF THE PHOTOGRAPHS

The accompanying colored photographs illustrate the overall appearance of the new *Azalea*. These photographs show the colors as true as it is reasonably possible to obtain in colored reproductions of this type. Colors in the photographs may differ slightly from the color values cited in the detailed botanical description, which accurately describe the colors of the new *Azalea.*

The photograph on the first sheet comprises a side perspective view of a typical flowering plant of 'YBAZ-2147'.

The photograph on the second sheet is a close-up view of a typical flower of 'YBAZ-2147'.

DETAILED BOTANICAL DESCRIPTION

The aforementioned photographs and following observations and measurements describe plants grown in Alva, Fla. with three plants per 15-cm containers, in a polypropylene-covered shade house during the autumn and under commercial production conditions. During the production of the plants, day temperatures ranged from 13° C. to 37° C. and night temperatures ranged from 0° C. to 26° C. Plants were pinched at planting, pinched a second time about twelve weeks later, and then pinched a third time about twelve weeks after the second pinch. After sufficient flower bud development, plants were cooled at 3° C. to 5° C. for about four weeks to break flower bud dormancy. Plants were subsequently forced into flower under commercial production conditions in a polyethylene-covered greenhouse. Plants used for the photographs and description were about one year old. In the following description, color references are made to The Royal Horticultural Society Colour Chart, 1995 Edition, except where general terms of ordinary dictionary significance are used.

Botanical classification: *Rhododendron hybrida* 'YBAZ-2147'.

Commercial classification: Evergreen greenhouse-forcing type *Azalea*.

Parentage: Naturally-occurring whole plant mutation of the *Rhododendron hybrida* cultivar YBAZ1812, disclosed in U.S. Pat. No. 16,499.

Propagation:

*Type.*—By terminal vegetative cuttings.

*Time to initiate roots.*—Summer: About five weeks at temperatures of 24° C. Winter: About six weeks at temperatures of 24° C.

*Time to produce a rooted young plant.*—Summer: About nine weeks at temperatures of 24° C. Winter: About eleven weeks at temperatures of 24° C.

*Root description.*—Fine, fibrous, and white in color.

*Rooting habit.*—Freely branching; moderately dense.

Plant description:

*Plant form and growth habit.*—Perennial, evergreen; uniform and outwardly spreading plant habit; broad inverted triangle; moderately vigorous growth habit. Densely foliated; full and bushy plants. Uniform and freely flowering habit with numerous fully double flowers per plant.

*Branching habit.*—Freely branching; about five to six primary lateral branches develop after the initial pinch (removal of terminal apex); numerous secondary and tertiary branches develop after the sequential second and third pinches.

*Plant height, soil level to top of flowers.*—About 23 cm.

*Plant diameter, area of spread.*—About 43 cm.

*Lateral branch description.*—Length: About 20 cm. Diameter at base: About 6 mm. Internode length: About 1.4 cm. Strength: Strong. Texture, developing: Pubescent, fine brown hairs. Texture, mature: Woody; pubescent, fine brown hairs. Color, developing: Close to 144A. Color, mature: Close to 165A.

*Foliage description.*—Arrangement: Alternate, single. Foliage retention: Very good foliage retention on plants of the new *Azalea* that have been in a box for six weeks during the cooling treatment. Length: About 5.1 cm. Width: About 2.2 cm. Shape: Mostly elliptic. Apex: Cuspidate to mucronate. Base: Attenuate. Margin: Entire. Venation pattern: Pinnate. Texture, upper and lower surfaces: Sparsely pubescent; leathery, tough. Color: Developing and fully expanded foliage, upper surface: Close to 147A; venation, close to 147A, towards the base, close to 146A. Developing and fully expanded foliage, lower surface: Close to 147B; venation, close to 146A to 146B. Petiole: Length: About 1.1 cm. Diameter: About 3 mm. Texture, upper and lower surfaces: Pubescent. Color, upper and lower surfaces: Close to 146B to 146C.

Flower description:

*Natural flowering season.*—Spring after sufficient cool period. If forced, plants typically flower about 29 days after a four-week cooling treatment; relatively rapid flowering response. Flowers persistent.

*Flower arrangement and appearance.*—Flowers arranged singly at terminals with usually about three to four flowers per apex; uniform and freely flowering habit. Flowers face upward or outward.

*Flower appearance.*—Flowers rotate and rose-like; fully double flower form with a single outer whorl of petals and two of four inner whorls of petaloids (transformed stamens).

*Postproduction longevity.*—Excellent postproduction longevity; under interior conditions, plants maintain good flower substance for about five weeks.

*Fragrance.*—None detected.

*Flower diameter.*—About 7.5 cm.

*Flower depth.*—About 3.5 cm.

*Flower bud (before showing color).*—Length: About 1.7 cm. Diameter: About 8 mm. Shape: Ovoid. Color: Close to 146A to 146B.

*Petals/petaloids.*—Arrangement: Fully double flower form; one outer whorl with about five imbricate petals and two to four inner whorls each with about five imbricate petaloids (transformed stamens); petals and petaloids fused at the base. Numerous whorls of petals and petaloids give a full, rose-like appearance to the flower. Petaloids variable in size and shape. Length, petals: About 4.4 cm. Width, petals: About 4 cm. Length, petaloids, center whorl: About 3.8 cm. Width, petaloids, center whorl: About 3 cm. Length, petaloids, inner whorl: About 3.1 cm. Width, petaloids, inner whorl: About 2.5 cm. Shape, petals and petaloids: Beyond fused base, roughly spatulate with rounded apex. Margin, petals and petaloids: Entire; smooth. Texture, petals and petaloids, upper and lower surfaces: Smooth, glabrous; velvety. Color, petals and petaloids: When opening and fully opened, lower surface: Close to 49A tinted with close to 50A. Color becoming closer to 49B to 49C with development. When opening and fully opened, lower surface: Close to 49A.

*Sepals.*—Arrangement: Five in a single whorl, fused; subtending the petals. Length: About 5 mm. Width: About 3 mm. Shape: Ovate to deltoid. Apex: Acute. Base: Fused. Texture, upper and lower surfaces: Pubescent. Color, upper surface: Close to 144A. Color, lower surface: Close to 146A.

*Peduncles.*—Length: About 2 cm. Diameter: About 2 mm. Angle: Mostly upright. Strength: Flexible; strong. Texture: Very pubescent. Color: Close to 144A.

*Reproductive organs.*—Androecium: None observed, typically all stamens transformed into petaloids. Gynoecium: Quantity of pistils per flower: Typically one. Pistil length: About 8 mm. Style length: About 4 mm. Style color: Close to 144A. Stigma shape: Rounded to flattened. Stigma diameter: About 2 mm. Stigma color: Close to 144A. Ovary color: Close to 146A; heavily whiskered.

*Seed/fruit.*—Seed and fruit development have not been observed.

Weather/temperature tolerance: Plants of the new *Azalea* have been observed to be very tolerant to rain and wind. Plants of the new *Azalea* have been observed to tolerate temperatures from about 0° C. to about 38° C.

Disease/pest resistance: Plants have not been observed to be resistant to pathogens and pests common to *Azaleas*.

It is claimed:

1. A new and distinct cultivar of *Azalea* plant named 'YBAZ-2147' as illustrated and described.

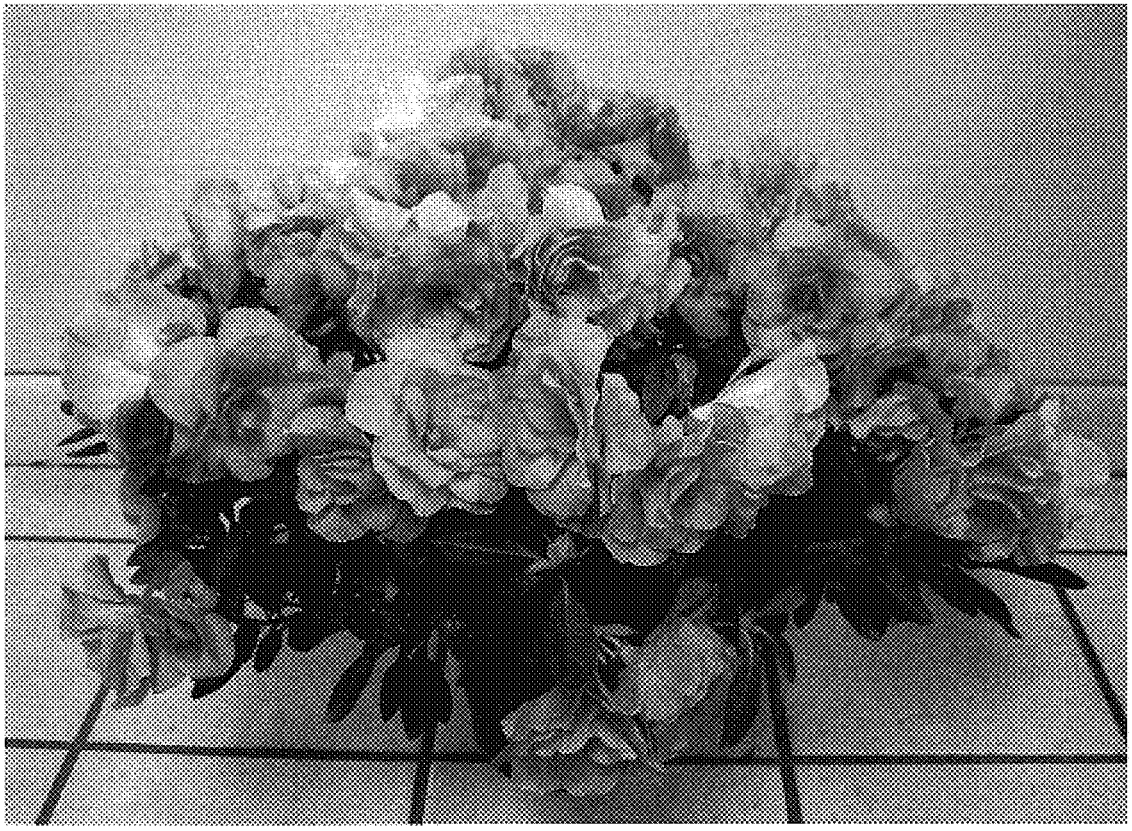

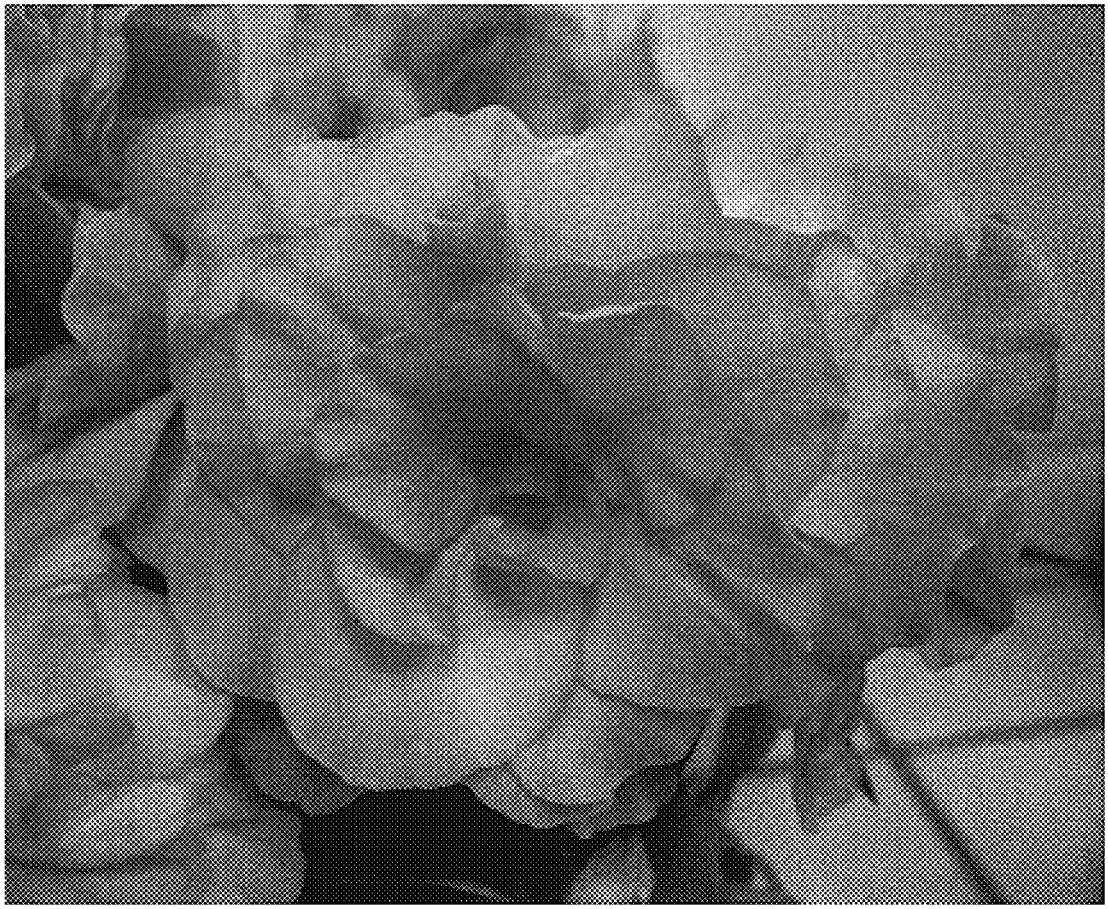

* * * * *